United States Patent [19]
Groot

[11] 4,424,811
[45] Jan. 10, 1984

[54] PINCHING DEVICE FOR SURGICAL PURPOSES

[76] Inventor: Gerrit S. Groot, No. 13, Nobeldreef, 2871 LA Schoonhoven, Netherlands

[21] Appl. No.: 345,664

[22] Filed: Feb. 4, 1982

Related U.S. Application Data

[63] Continuation of Ser. No. 147,187, May 6, 1980, abandoned.

[30] Foreign Application Priority Data

May 7, 1979 [NL] Netherlands .......................... 7903570

[51] Int. Cl.³ .............................................. A61B 17/12
[52] U.S. Cl. .................................... 128/346; 128/325; 128/354; 24/528; 81/354
[58] Field of Search ............... 128/346, 321, 322, 325, 128/354; 24/263 R; 251/6, 8; 81/341, 342, 347, 352, 355, 356, 373, 407, 353, 354, 43

[56] References Cited
U.S. PATENT DOCUMENTS 3,308,518  3/1967  Waxelbaum ....................... 24/263 R

FOREIGN PATENT DOCUMENTS 336526  5/1921  Fed. Rep. of Germany ...... 128/346
455644  2/1928  Fed. Rep. of Germany ...... 128/346

OTHER PUBLICATIONS

Surg. Gynec. and Obstr., vol. 68, Jan. 1939, p. 11, No. 2A.

*Primary Examiner*—Michael H. Thaler
*Attorney, Agent, or Firm*—Diller, Ramik & Wight

[57] ABSTRACT

The invention relates to a pinching device for surgical purposes comprising two parallel jaw elements having each a supporting part, one of which is provided with a pin at right angles thereto and the other having a sleeve mounted at right angles thereto and fitting around said pin.

The pinching device according to the invention is characterized in that one supporting part is provided with a guide pin and the other has a bore receiving said pin located in the same plane as the first-mentioned pin and the sleeve.

9 Claims, 3 Drawing Figures

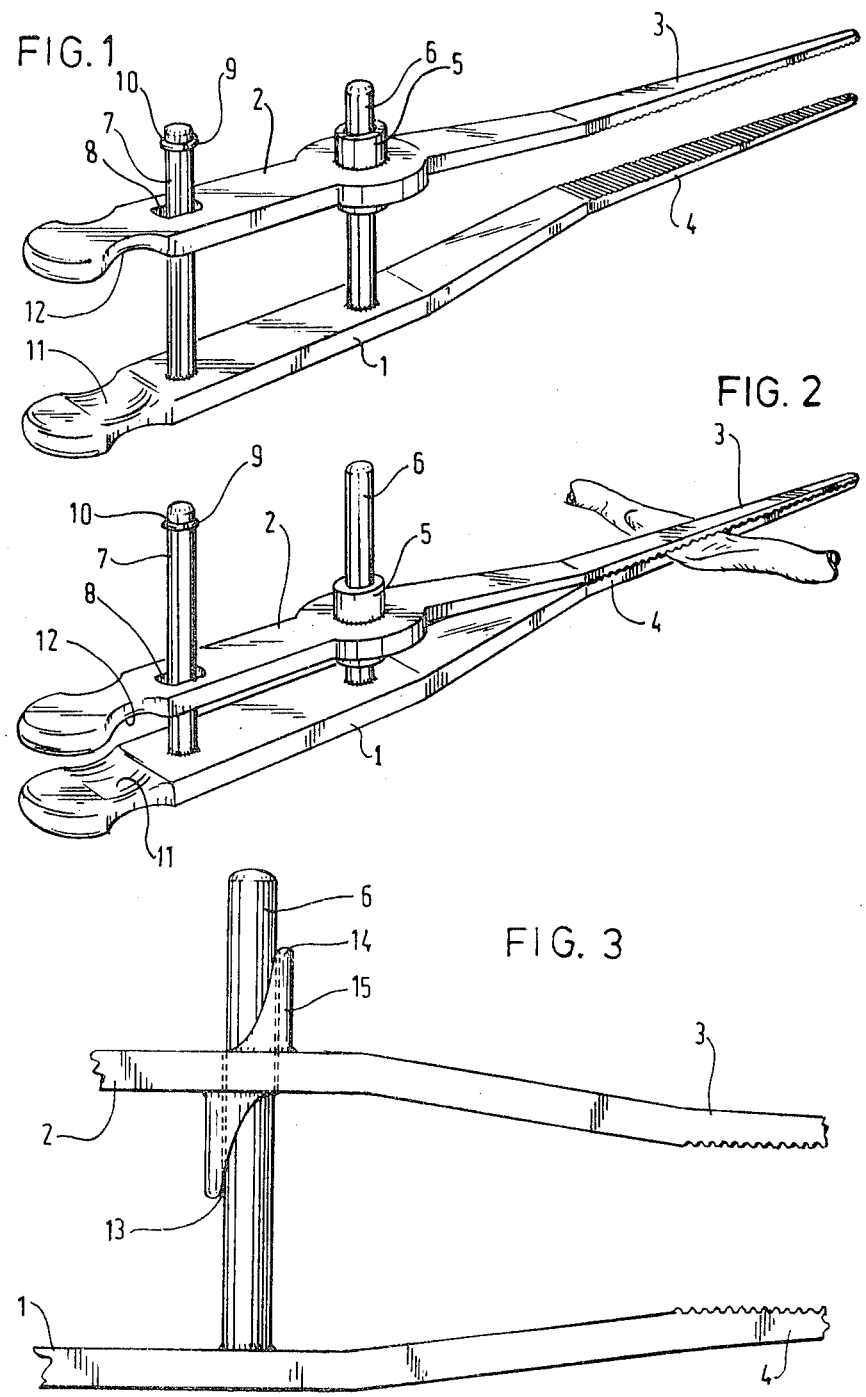

PINCHING DEVICE FOR SURGICAL PURPOSES

This application is a continuation, of application Ser. No. 147,187, filed May 6, 1980, now abandoned.

The invention relates to a pinching device for surgical purposes comprising two parallel jaw elements having each a supporting part, one of which is provided with a pin at right angles thereto and the other having a sleeve mounted at right angles thereto and fitting around said pin.

Such a pinching device is known from German patent application 1,791,102. This known pinching device is provided with a hollow pin, which is slidable in a concentric sleeve, and with a compression spring arranged in said pin and in said sleeve and acting on said parts in a manner such that they are urged away from one another and hence the two jaw elements are urged towards one another.

In order to maintain the two jaw elements at a given distance from one another an expedient, for example, surgical pincers is required with a fixing device. Since it is practically not possible to partially pinch off and to completely pinch off blood vessels by means of such a pinching device without damage to the vessels, and since displacement of this pinching device is only possible in given increments and reopening is accompanied by an initial additional closure of the jaw elements due to the structure of the surgical pincers to be used, there is a need for a pinching device which does not exhibit these disadvantages.

The invention provides a pinching device of the kind set forth, which is characterized in that one supporting part is provided with a guide pin and the other has a bore receiving said pin located in the same plane as the first-mentioned pin and the sleeve. Such a construction provides an improved feel for use even with gloved hands. Moreover, the adjustability is continuous and re-opening is possible without first closing the jaws further.

With a view to the unavoidable amount of play between the components it is advisable to locate the sleeve on that side of a supporting part, which holds a jaw element in order to avoid an appreciable increase in the given distance between the jaw elements after being manually adjusted.

In manufacture and in use it is preferred to fasten the two pins to the same supporting part.

In order to avoid unintentional removal of the parts from one another it is desirable to provide one of the pins near its free end with a thickened portion. The end of the pin passed through the sleeve or the bore is thus prevented from leaving the sleeve or the bore. During cleaning and disinfection after use of the pinching device it is desirable to separate the parts from one another in order to give access to cavities and gaps. To this end the thickened portion is constructed in the form of a circlip located in an uninterrupted groove in the pin. By removing this circlip, but preferably by proportioning this circlip so that it can pass resiliently through the bore or the sleeve by exerting a great force, that is to say, a force definitely exceeding the force exerted in normal use, the two parts of the pinching device can be separated from one another in a simple manner. For opening the pinching device it is only necessary to move away from one another the ends of the supporting parts remote from the jaw elements: for facilitating this manipulation it is advisable to provide a finger hole at the free end of each supporting part on the side facing the other part. For the same purpose it is also advisable to arrange the supporting parts at a larger distance from one another than the jaw elements in the plane in which they are relatively displaceable. The latter structure ensures that even when the pinching device is completely closed the supporting parts are not in contact with one another and hence remain readily accessible for opening the pinching device.

The pinching device is retained in the adjusted position by the stress of the object located between the jaw elements. Owing to this stress a tilting moment is exerted on the pin with respect to the sleeve so that owing to the friction produced between them a relative displacement is prevented. Obviously parts of the sleeve are essentially inoperative, so that it is possible to partly remove the sleeve on one supporting part on the side facing the other supporting part and the associated jaw element and on the side remote therefrom. By this modification weight of material can be saved.

The invention will be described more fully with reference to a drawing in which show FIG. 1 is a perspective view of a pinching device in accordance with the invention, FIG. 2 a perspective view in the operational position of a preferred embodiment of the pinching device of FIG. 1, and FIG. 3 an enlarged detail of a modified embodiment of the pinching device in accordance with the invention.

FIGS. 1 and 2 show a surgical pinching device comprising two elongated supporting parts 1, 2 having at corresponding ends each one jaw element 4, 3. Although in FIG. 1 the jaw elements 4, 3 are shown as prolongations of the supporting parts 1, 2, they may alternatively be at an obtuse angle, which is interesting for various uses. One supporting part 1 is provided with two parallel, smooth pins 6, 7 extending through holes in the other supporting part 2. In the hole nearest the jaw elements 3, 4 is fixedly arranged a sleeve 5, through which the pin 6 can slide with a minor amount of clearance. The other hole is an elongated bore 8, through which the guide pin 7 can pass with ample clearance. In this way the two supporting parts 1, 2 can be moved away from and towards one another, whilst their parallel position is maintained so that also the forcing surfaces of the jaw elements 3, 4 are displaceable towards and away from one another in parallel relationship. For this displacement a force has to be exerted on the two supporting parts 1, 2 near the pin 6 and the sleeve 5.

An object clamped between the jaw elements 3, 4 will exert thereon a reactive force resulting in an opposite tilting moment on the sleeve 5 and the pin 6 so that owing to the friction between them they cannot be displaced by said reactive force. If the pinching force has to be mitigated it is only necessary to move away from one another the ends of the supporting parts 1, 2 remote from the jaw elements 3, 4, which is facilitated by the cavities 11, 12 provided near said ends on the proximal sides for receiving a finger.

In order to avoid disengagement of the two parts one of the pins 7 has a thickened portion constructed in the embodiment shown in the form of a circlip 9 located in an uninterrupted groove 10 and having an outer diameter which exceeds the smaller dimension of the bore 8. However, for facilitating cleaning and sterilisation the circlip 9 can pass through the bore 8 whilst its diameter can be reduced by exerting a greater force on the pinching device than is applied in normal use. During mounting an inverse manipulation can be carried out.

Since for maintaining the clamping force of the jaw elements 3, 4 only the points 13, 14 of the sleeve 15 as shown in FIG. 3 are important, the portions facing the other supporting part 1 and the associated jaw element 3 and the portion remote therefrom i.e. the diagonally opposite portion can be omitted. This causes a saving of weight and it facilitates closure of the pinching device, when the closing force is not exerted directly near the pin 6 and the sleeve 15, but is applied further to the left in FIG. 3.

What I claim is:

1. A surgical clamp comprising, in combination:
    a pair of elongate supporting parts disposed in spaced opposition and a pair of jaw elements disposed in parallel opposition, each jaw element merging with one end of a corresponding supporting part; and
    means for freely guiding said jaw elements for manual movement toward and away from each other and for frictionally holding the jaw members clamped upon an anatomical member such as a blood vessel with and in response to a pressure which has been manually established while allowing subsequent manual release of such frictional holding without first closing the jaw elements further, said means comprising a circular pin anchored to and upstanding from one of said supporting parts and passing through the other supporting part, an elongated, circular sleeve carried by said other supporting part and through which said pin passes with a minor amount of clearance, said sleeve having mutually inwardly facing inner surfaces, one adjacent each of its opposite ends, which frictionally engage and hold onto said pin due to slight relative tilting between said sleeve and pin caused by the pressure exerted by said jaw elements on the anatomical member, and a second upstanding pin anchored on one of said supporting parts and passing through an opening in the other part for preventing relative rotation of the parts about the axis of the pin first mentioned while permitting said slight relative tilting, said supporting parts having portions on that side of said first pin remote from said jaw elements which are spaced apart from each other sufficient in that region adjacent said sleeve and even when the jaw elements are engaged together to permit insertion of a finger therebetween to allow said sleeve to be forcibly slid along said first pin despite said frictional engagement and thereby allow the frictional holding between said first pin and said sleeve to be released without first closing the jaw elements further.

2. A surgical clamp as defined in claim 1 wherein said circular pin is anchored to its supporting part closely adjacent that end thereof which merges with its corresponding jaw element.

3. A surgical clamp as defined in claim 1 or 2 wherein both of said pins are anchored to the same supporting part.

4. A surgical clamp as defined in claim 3 wherein said portions of the supporting parts are the free ends thereof remote from said jaw elements and such portions present mutually facing concavities which readily accommodate a surgeon's gloved finger.

5. A surgical clamp as defined in claim 1 or 2 wherein said second pin is provided with an enlarged portion adjacent its free end which is larger than said opening.

6. A surgical clamp as defined in claim 5 wherein said second pin is provided with a circumferential groove adjacent said free end thereof and said enlarged portion is in the form of a circlip in said groove which may be forced through said opening.

7. A surgical clamp as defined in claim 6 wherein said portions of the supporting parts are the free ends thereof remote from said jaw elements and such portions present mutually facing concavities which readily accommodate a surgeon's gloved finger.

8. A surgical clamp as defined in claim 1 or 2 wherein said portions of the supporting parts are the free ends thereof remote from said jaw elements and such portions present mutually facing concavities which readily accommodate a surgeon's gloved finger.

9. A surgical clamp as defined in claim 1 or 2 wherein the opposite ends of said sleeve are cut away to expose said mutually inwardly facing inner surfaces thereof.

* * * * *